United States Patent

Lipshitz et al.

[11] Patent Number: 5,814,103
[45] Date of Patent: Sep. 29, 1998

[54] INTRAOCULAR LENS AND TELESCOPE WITH MATING FASTENERS

[75] Inventors: Isaac Lipshitz, Herzliya Pituach; Yosef Gross, Moshav Mazor; Gideon Dotan, Yehud; Eli Aharoni, Rishon le Zion, all of Israel

[73] Assignee: Visioncare Ltd., Yehud, Israel

[21] Appl. No.: 7,381

[22] Filed: Jan. 15, 1998

[51] Int. Cl.⁶ ............................................. A61F 2/16
[52] U.S. Cl. ............................................. 623/6
[58] Field of Search ..................................... 623/6

[56] References Cited

U.S. PATENT DOCUMENTS

| | | | |
|---|---|---|---|
| 4,074,368 | 2/1978 | Levy, Jr. et al. | 623/6 |
| 4,731,078 | 3/1988 | Stoy et al. | 623/6 |
| 4,759,761 | 7/1988 | Portnoy | 623/6 |
| 4,863,468 | 9/1989 | Feinbloom et al. | 623/6 |
| 5,275,623 | 1/1994 | Sarfarazi | 623/6 |
| 5,354,335 | 10/1994 | Lipshitz et al. | 623/6 |
| 5,391,202 | 2/1995 | Lipshitz et al. | 623/6 |

*Primary Examiner*—Mary Beth Jones
*Attorney, Agent, or Firm*—Darby & Darby

[57] ABSTRACT

An intraocular lens implant including an intraocular lens, a telescope, and at least one mechanical fastener that fixedly attaches the telescope to the lens. Either the lens or the telescope may be integrally formed with the at least one mechanical fastener. For example, the lens may be formed with a female fastener which mates with a corresponding male fastener formed on the telescope. Alternatively, the lens may be formed with a male fastener which mates with a corresponding female fastener formed on the telescope.

17 Claims, 3 Drawing Sheets

INTRAOCULAR LENS AND TELESCOPE WITH MATING FASTENERS

FIELD OF THE INVENTION

The present invention relates generally to intraocular lens (IOL) implants and particularly to an intraocular lens and telescope constructed with mating mechanical fasteners.

BACKGROUND OF THE INVENTION

Intraocular inserts comprising telescopes are known. European Published Patent Application EP-A-212616 describes an intraocular lens that includes an anterior convex lens and a posterior concave lens. The contour of the lens can be selectively changed by varying the amount of fluid therein in order to change its refractive power. The lens is intended solely as a replacement for the natural lens of the eye.

U.S. Pat. No. 4,074,368 also describes an intraocular lens that includes an anterior convex lens and a posterior concave lens with high magnification proposed for the relief of conditions such as macular degeneration and diabetic retinopathy. The lens has many relatively low power lens surfaces arranged in a relatively long lens assembly which extends, when implanted, through almost the entire depth of the eye, from the pupil nearly to the retina. Implanting such a lens would necessitate major surgery. Moreover, the proposed lens does not provide a replacement for the natural lens for a wide field of view.

French Published Patent Application 2,666,735 describes an implant that includes a lens-shaped optical portion and a fastening assembly for securing the implant in the eye. The optical portion includes at least one closed internal cavity which contains a fluid or vacuum, forming a refraction chamber changing the optical properties of the lens.

Applicant/assignee's U.S. Pat. Nos. 5,354,335 and 5,391,202, the disclosures of which are incorporated herein by reference, describe intraocular inserts with a positive (converging) lens facing the anterior side of the eye and a negative (diverging) lens facing the posterior side, the two lenses forming a Galilean telescopic system. In U.S. Pat. No. 5,354,335, the lenses are assembled in a body member, the positive lens being generally flush with the anterior face of the body member. The negative lens may either be flush with the posterior face of the body member, or may project posteriorly therefrom. The body member anterior and/or posterior faces may be convex. In U.S. Pat. No. 5,391,202, the positive lens projects anteriorly from the anterior face of the body member which is preferably a soft lens constructed from a material such as a silicone. In U.S. patent application Ser. No. 08/882,972, the disclosure of which is incorporated herein by reference, the present applicant/assignee discloses a further intraocular implant comprising a telescope body having an anterior end and a posterior end and including one or more windows sealed to the telescope body at the anterior end and/or the posterior end. There are at least two lenses disposed within the telescope body intermediate the anterior and posterior ends. The lenses may be a so-called reverse Galilean telescope, i.e., a negative lens faces the anterior side of the eye while a positive lens faces the posterior side of the eye. One of the features of the system is that the lenses are doublet lenses. The windows may be formed without optical power, or alternatively, may comprise a prism.

In U.S. patent application Ser. No. 08/882,973, the disclosure of which is incorporated herein by reference, the present applicant/assignee discloses yet another intraocular implant comprising a telescope (either Galilean or reverse Galilean) which extends through at least a portion of a lens capsule of the eye and forwardly thereof toward the anterior side of the eye, the telescope not penetrating the vitreous of the eye. The intraocular lens implant is supported within the lens capsule by loops, in the absence of a lens within the lens capsule. One of the features of the system is that the telescope may be tilted such that light from outside the eye is focused by the telescope on a low resolution but operative section of the retina. Other optional features of the system include one or more lenses having a graded index of refraction, holographic (diffusing) lenses, and/or doublet lenses which help prevent chromatic aberrations. The patent application also discloses a method for manufacturing an intraocular insert telescope employing laser fusing to join the lenses to the telescope body. Alternatively or additionally, the method employs glass particles having a low temperature melting point as a joining medium.

None of the prior art, however, provides a solution to the following problem. Galilean telescopic IOL's are designed to correct problems stemming from central field defects, such as those caused by macular degeneration (e.g., atrophic or exudative), chorioretinitis of the macula, central serous chorioretinopathy, or ischemia, for example. Reverse Galilean telescopic IOL's are designed to correct problems stemming from peripheral field defects, such as those caused by retinitis pigmentosa, primary or metastatic central nervous system tumors or glaucoma, for example. The majority of cases of central or peripheral field defects manifest themselves only after cataracts or other disorders which warrant implantation of an IOL. Thus, usually the need for a telescope or telescopic IOL arises after a regular IOL has already been implanted. It is difficult and possibly damaging to remove the regular IOL after years of service and implant in its place a telescopic IOL.

SUMMARY OF THE INVENTION

The present invention seeks to provide an improved telescopic lens system extending from an IOL which solves the above mentioned problem. A system is provided whereby a "regular" IOL can be implanted and a telescope added thereto afterwards without need for removing the IOL from the eye. The primary purpose of the present invention is to allow attachment of the telescope to the lens after months or years of service. However, the present invention also provides a novel system for initially installing the IOL together with the telescope, in two convenient steps: first the lens and then the telescope.

Specifically, the present invention provides an intraocular lens and telescope constructed with mating mechanical fasteners. After implantation in the eye, the telescope is quickly and simply fastened to the lens.

There is thus provided in accordance with a preferred embodiment of the present invention an intraocular lens implant including an intraocular lens, a telescope, and at least one mechanical fastener that fixedly attaches the telescope to the lens.

In accordance with a preferred embodiment of the present invention at least one of the lens and the telescope is integrally formed with the at least one mechanical fastener.

Additionally in accordance with a preferred embodiment of the present invention the lens is formed with a female fastener which mates with a corresponding male fastener formed on the telescope. Alternatively in accordance with another preferred embodiment of the present invention the lens is formed with a male fastener which mates with a corresponding female fastener formed on the telescope.

Preferably the fastener of the telescope is formed at an end of the telescope.

Further in accordance with a preferred embodiment of the present invention the male fastener includes at least one stud and the female fastener is a groove formed by a first socket connected by a notch to a second socket, the notch being narrower than the sockets, wherein the at least one stud is fixedly inserted into the second socket by first inserting the at least one stud into the first socket and forcibly passing the at least one stud past the notch into the second socket.

Still further in accordance with a preferred embodiment of the present invention the fasteners are threadably engageable with each other.

Additionally in accordance with a preferred embodiment of the present invention the male fastener includes at least one protrusion and wherein the female fastener includes at least one tab, wherein rotation of the telescope with respect to the lens snugly and fixedly mates the at least one protrusion with the at least one corresponding tab.

In accordance with a preferred embodiment of the present invention the male fastener includes a flange and wherein the female fastener includes at least one elastic tongue, herein the flange snaps together with the at least one tongue.

Further in accordance with a preferred embodiment of the present invention the at least one mechanical fastener is provided separately from the lens and the telescope.

Still further in accordance with a preferred embodiment of the present invention the telescope includes an end face which has a curvature to match a curvature of the lens.

The telescope may include an anteriorly positioned positive lens and a posteriorly positioned negative lens. Alternatively, the telescope may include an anteriorly positioned negative lens and a posteriorly positioned positive lens.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
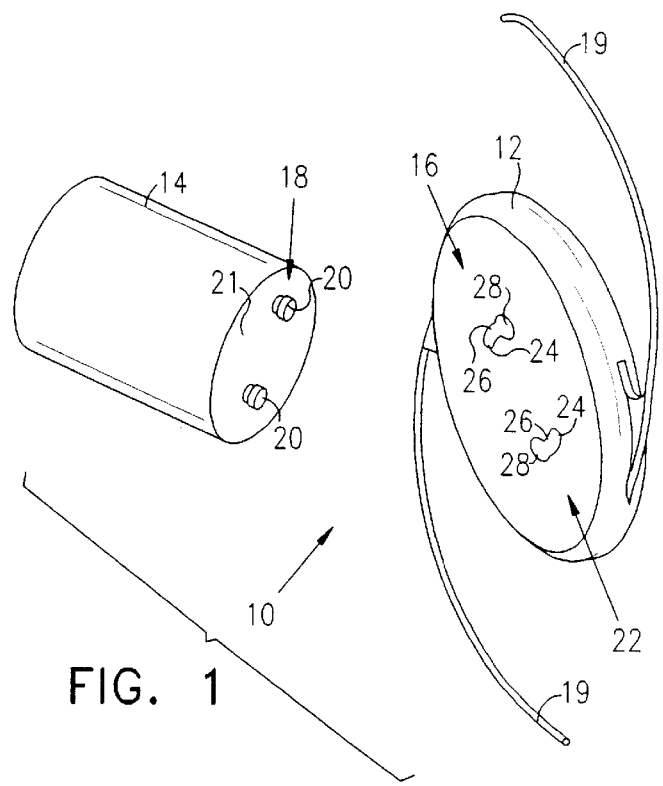
FIG. 1 is a simplified pictorial illustration of an intraocular lens implant with a telescope, constructed and operative in accordance with a preferred embodiment of the present invention, wherein the telescope has studs which mate with grooves in the lens.

Reference is now made to FIG. 1 which illustrates an intraocular lens implant 10 constructed and operative in accordance with a preferred embodiment of the present invention. Lens implant 10 includes an intraocular lens 12 and a telescope 14 formed with mating mechanical fasteners. In the embodiment illustrated in FIG. 1, lens 12 is formed with one or more female fasteners 16 and telescope 14 is formed with one or more corresponding male fasteners 18. Lens 12 is preferably formed with one or more haptics 19.

Telescope 14 may be constructed in accordance with the teachings of applicant/assignee's U.S. Pat. Nos. 5,354,335 and 5,391,202, or U.S. patent application Ser. Nos. 08/882,972 or 08/882,973. As described in these references, telescope 14 may be either Galilean (having an anteriorly positioned positive lens and a posteriorly positioned negative lens) or reverse Galilean (having an anteriorly positioned negative lens and a posteriorly positioned positive lens).

Figure 3:
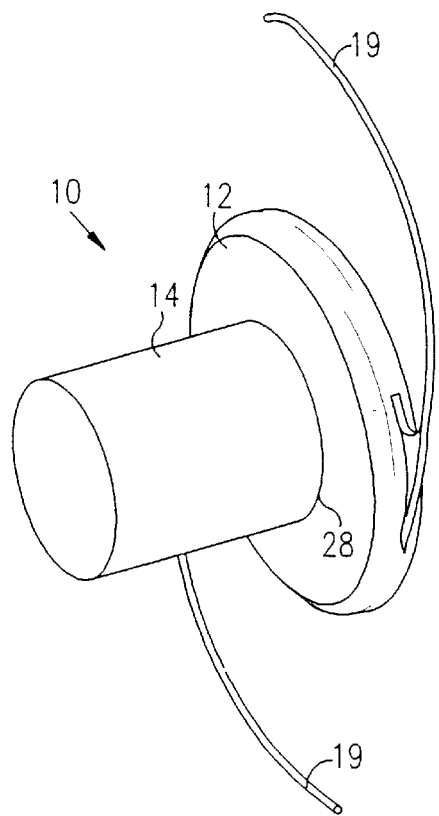
FIG. 3 is a simplified pictorial illustration of the intraocular lens implant assembled together with the telescope of either FIG. 1 or FIG. 2.

Male fastener 18 preferably includes one or more studs 20 protruding from an end 21 of telescope 14, and female fastener 16 includes one or more grooves 22 corresponding to studs 20. Each groove 22 is preferably formed by a first socket 24 connected by a notch 26 to a second socket 28. Notch 26 is preferably narrower than sockets 24 and 28 so that each stud 20 may be inserted into first socket 24, and then fixedly seated in second socket 28 by turning telescope 14 so as to forcibly pass stud 20 past notch 26. The outer dimension of stud 20, in the case of a cylindrical stud the diameter, and the material of stud are selected so that stud 20 is preferably slightly compressed as it passes through notch 26. A suitable material for stud 20, as well as for the rest of lens implant 10, is polymethylmethacrylate (PMMA), for example. The finished assembled implant 10 is shown in FIG. 3.

Figure 2:
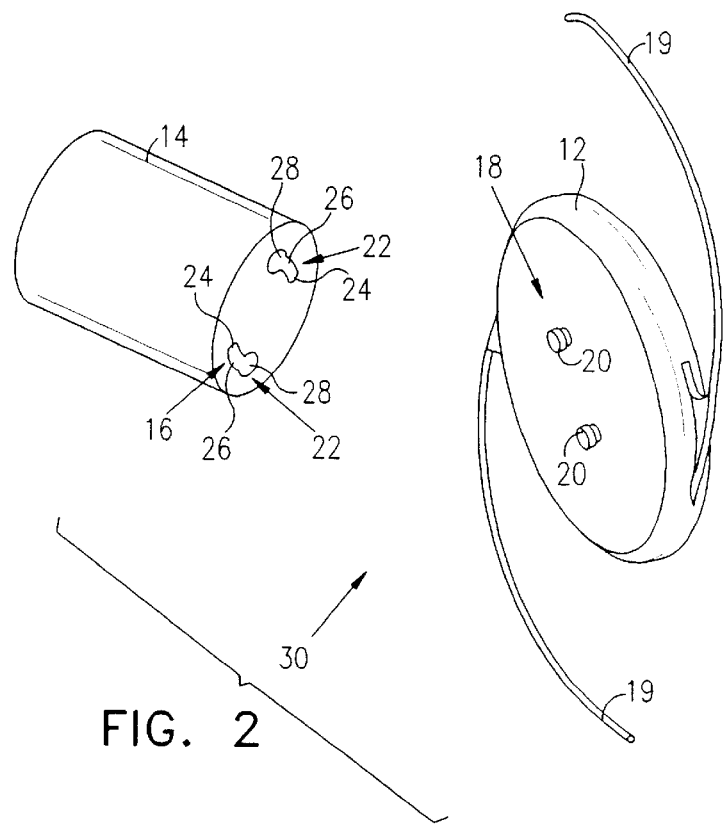
FIG. 2 is a simplified pictorial illustration of an intraocular lens implant with a telescope, constructed and operative in accordance with another preferred embodiment of the present invention, wherein the lens has studs which mate with grooves in the telescope.

Reference is now made to FIG. 2 which illustrates an intraocular lens implant 30 constructed and operative in accordance with another preferred embodiment of the present invention. Lens implant 30 is basically the same as lens implant 10 except that lens 12 is formed with male fasteners 18 which mate with the corresponding female fasteners 16 formed on telescope 14.

Figure 4:
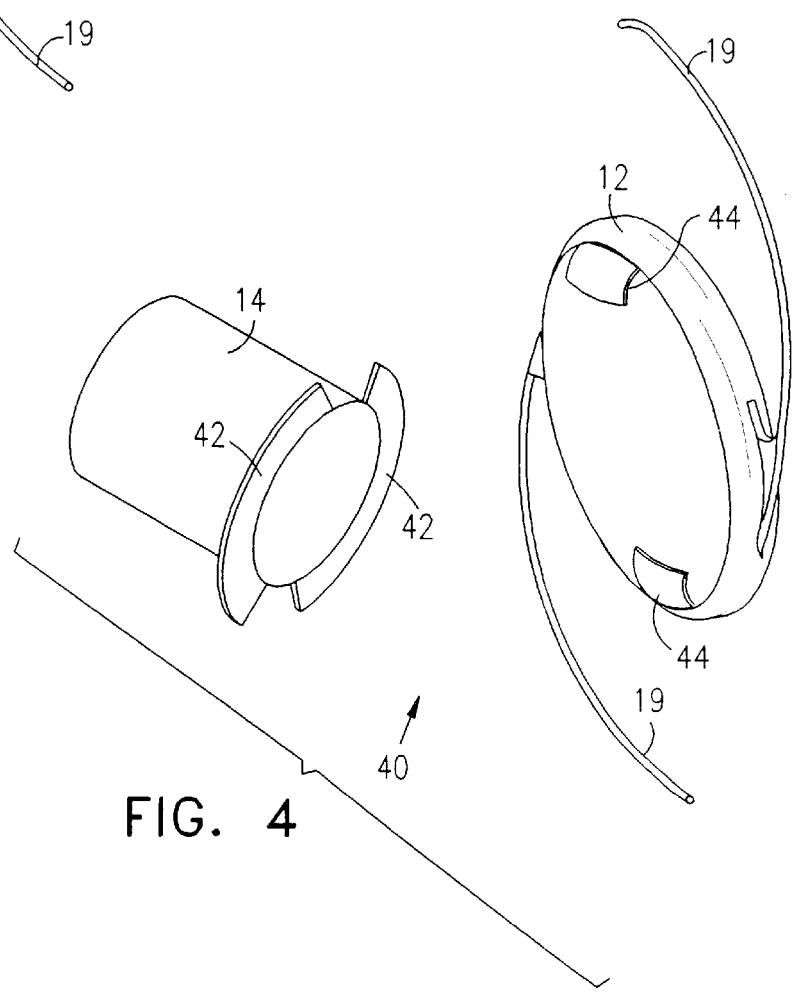
FIG. 4 is a simplified pictorial illustration of an intraocular lens implant with a telescope, constructed and operative in accordance with yet another preferred embodiment of the present invention, wherein the telescope has annular protrusions which mate with tabs formed on the lens.

Reference is now made to FIG. 4 which illustrates an intraocular lens implant 40 constructed and operative in accordance with yet another preferred embodiment of the present invention. Lens implant 40 is basically the same as lens implants 10 and 30 except that telescope 14 is formed with one or more annular protrusions 42 which snugly and fixedly mate with one or more tabs 44 formed on lens 12. Protrusions 42, preferably formed at an end of telescope 14, are forcibly slid under tabs 44 by suitably rotating telescope 14 and lens 12 with respect to each other. Protrusions 42 thus act as male fasteners and tabs 44 act as female fasteners. Of course, alternatively, the tabs could be formed on the telescope and the protrusions on the lens.

Figure 5:
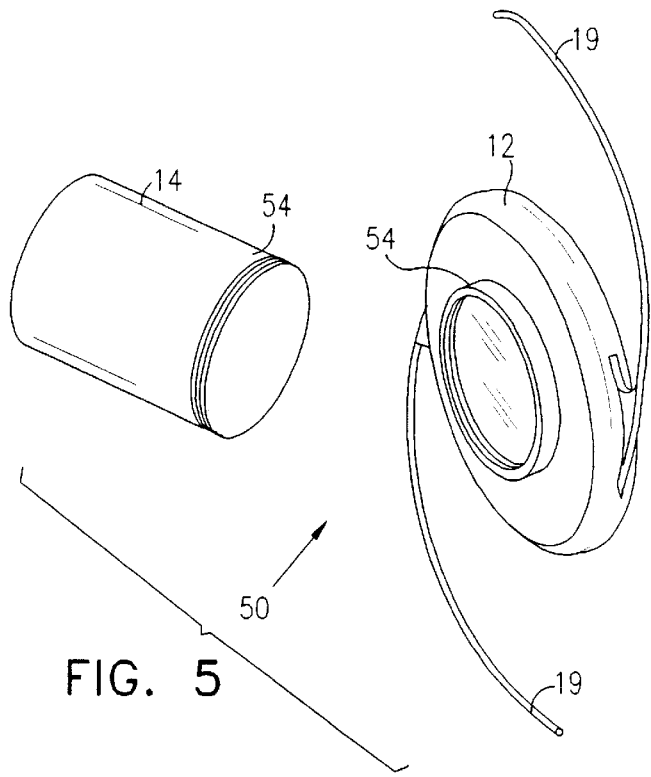
FIG. 5 is a simplified pictorial illustration of an intraocular lens implant with a telescope, constructed and operative in accordance with still another preferred embodiment of the present invention, wherein the telescope is formed with a male thread which mates with a corresponding female thread formed on the lens.

Reference is now made to FIG. 5 which illustrates an intraocular lens implant 50 constructed and operative in accordance with still another preferred embodiment of the present invention. Lens implant 50 is basically the same as lens implants 10 and 30 except that telescope 14 is formed with a male thread 52 which mates with a corresponding female thread 54 formed on lens 12. Of course, alternatively, the female thread could be formed on the telescope and the male thread on the lens.

Figure 6:
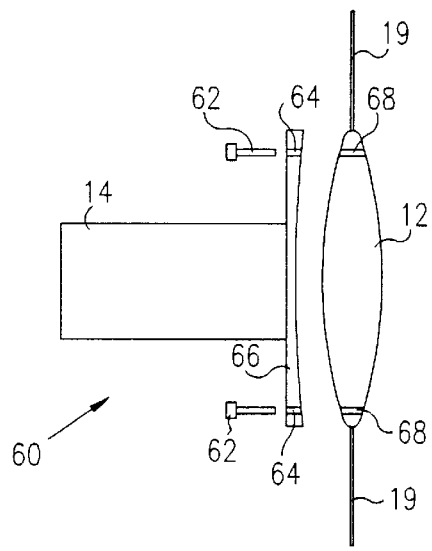
FIG. 6 is a simplified pictorial illustration of an intraocular lens implant with a telescope, constructed and operative in accordance with another preferred embodiment of the present invention, wherein the telescope is attached to the lens with separate mechanical fasteners.

Reference is now made to FIG. 6 which illustrates an intraocular lens implant 60 constructed and operative in accordance with another preferred embodiment of the present invention. Lens implant 60 is basically the same as lens implants 10 and 30 except that telescope 14 is attached to lens 12 with separate mechanical fasteners 62, such as screws. For purposes of example only, fasteners 62 may fit through holes 64 formed in a flange 66 of telescope 14 and mate with threaded holes 68 formed in lens 12. It is seen in FIG. 6 that telescope 14 may include an end face which has a curvature (e.g., concavity) to match a curvature of lens 12 (e.g., convexity). This feature, of course, may be provided in any of the other intraocular lens implants of the present invention.

Figure 7:
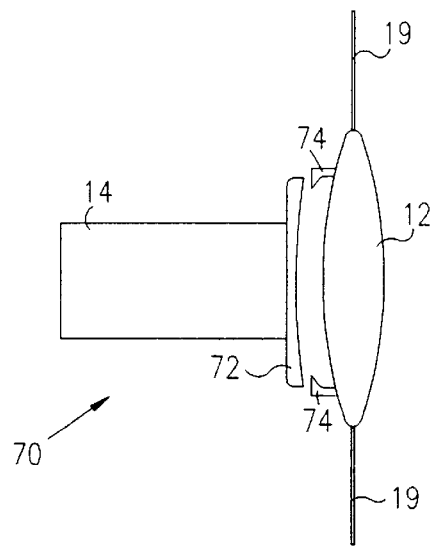
FIG. 7 is a simplified pictorial illustration of an intraocular lens implant with a telescope, constructed and operative in accordance with still another preferred embodiment of the present invention, wherein the telescope is formed with a flange which snaps together with elastic tongues formed on the lens.

Reference is now made to FIG. 7 which illustrates an intraocular lens implant 70 constructed and operative in accordance with another preferred embodiment of the present invention. Lens implant 70 is basically the same as lens implants 10 and 30 except that telescope 14 is formed with a flange 72 which snaps together with one or more elastic tongues 74 formed on lens 12. Of course, alternatively, the tongues could be formed on the telescope and the flange on the lens.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An intraocular lens implant comprising an intraocular lens, a telescope, and at least one mechanical fastener that fixedly attaches said telescope to said lens.

2. The implant according to claim 1 wherein at least one of said lens and said telescope is integrally formed with said at least one mechanical fastener.

3. The implant according to claim 1 wherein said lens is formed with a female fastener which mates with a corresponding male fastener formed on said telescope.

4. The implant according to claim 1 wherein said lens is formed with a male fastener which mates with a corresponding female fastener formed on said telescope.

5. The implant according to claim 1 and wherein said fastener of said telescope is formed at an end of said telescope.

6. The implant according to claim 3 and wherein said male fastener comprises at least one stud and said female fastener is a groove formed by a first socket connected by a notch to a second socket, said notch being narrower than said sockets, wherein said at least one stud is fixedly inserted into said second socket by first inserting said at least one stud into said first socket and forcibly passing said at least one stud past said notch into said second socket.

7. The implant according to claim 3 and wherein said fasteners are threadably engageable with each other.

8. The implant according to claim 3 and wherein said male fastener comprises at least one protrusion and wherein said female fastener comprises at least one tab, wherein rotation of said telescope with respect to said lens snugly and fixedly mates said at least one protrusion with said at least one corresponding tab.

9. The implant according to claim 3 and wherein said male fastener comprises a flange and wherein said female fastener comprises at least one elastic tongue, wherein said flange snaps together with said at least one tongue.

10. The implant according to claim 1 wherein said at least one mechanical fastener is provided separately from said lens and said telescope.

11. The implant according to claim 1 and wherein said telescope comprises an end face which has a curvature to match a curvature of said lens.

12. The implant to claim 1 and wherein said telescope comprises an anteriorly positioned positive lens and a posteriorly positioned negative lens.

13. The implant according to claim 1 and wherein said telescope comprises an anteriorly positioned negative lens and a posteriorly positioned positive lens.

14. The implant according to claim 4 and wherein said male fastener comprises at least one stud and said female fastener is a groove formed by a first socket connected by a notch to a second socket, and said notch being narrower than said sockets, wherein said at least one stud is fixedly inserted into said second socket by first inserting said at least one stud into said first socket and forcibly passing said at least one stud past said notch into said second socket.

15. The implant according to claim 4 and wherein said fasteners are threadably engageable with each other.

16. The implant according to claim 4 and wherein said male fastener comprises at least one protrusion and wherein said female fastener comprises at least one tab, wherein rotation of said telescope with respect to said lens snugly and fixedly mates said at least one protrusion with said at least one corresponding tab.

17. The implant according to claim 4 and wherein said male fastener comprises a flange and wherein said female fastener comprises at least one elastic tongue, wherein said flange snaps together with said at least one tongue.

* * * * *